United States Patent
Chovanda et al.

(10) Patent No.: US 9,861,747 B2
(45) Date of Patent: Jan. 9, 2018

(54) METHOD AND SYSTEM FOR MANAGEMENT OF DIABETES WITH A GLUCOSE MONITOR AND INFUSION PUMP TO PROVIDE FEEDBACK ON BOLUS DOSING

(71) Applicant: LifeScan, Inc., Milpitas, CA (US)

(72) Inventors: Sweta Chovanda, Exton, PA (US); Carlos Omar Morales, West Chester, PA (US)

(73) Assignee: LifeScan, Inc., Wayne, PA (US)

( * ) Notice: Subject to any disclaimer, the term of this patent is extended or adjusted under 35 U.S.C. 154(b) by 930 days.

(21) Appl. No.: 14/098,353

(22) Filed: Dec. 5, 2013

(65) Prior Publication Data
US 2015/0157792 A1    Jun. 11, 2015

(51) Int. Cl.
*A61M 31/00*    (2006.01)
*A61M 5/172*    (2006.01)
*G06F 19/00*    (2011.01)

(52) U.S. Cl.
CPC ......... *A61M 5/1723* (2013.01); *G06F 19/345* (2013.01); *G06F 19/3468* (2013.01); *A61M 2205/3569* (2013.01); *A61M 2205/502* (2013.01)

(58) Field of Classification Search
CPC .... A61M 2205/3569; A61M 2205/502; A61M 5/1723; A61M 5/14; A61M 5/142; A61M 2005/14208; A61M 5/16877
USPC ....................................... 604/504
See application file for complete search history.

(56) References Cited

U.S. PATENT DOCUMENTS

| 6,852,104 B2 | 2/2005 | Blomquist |
| 6,872,200 B2 | 3/2005 | Mann et al. |
| 7,060,059 B2 | 6/2006 | Keith et al. |
| 7,276,029 B2 | 10/2007 | Goode, Jr. et al. |
| 7,815,602 B2 | 10/2010 | Mann et al. |
| 7,819,843 B2 | 10/2010 | Mann et al. |
| 8,579,854 B2 * | 11/2013 | Budiman ........... A61B 5/14532 604/66 |
| 2010/0262434 A1 | 10/2010 | Shaya |
| 2010/0274592 A1 | 10/2010 | Nitzan et al. |

(Continued)

FOREIGN PATENT DOCUMENTS

| WO | 2011091238 A1 | 7/2011 |
| WO | 2011104517 A2 | 9/2011 |
| WO | 2012051344 A2 | 4/2012 |

OTHER PUBLICATIONS

Percival et al., "Closed-Loop Control and Advisory Mode Evaluation of an Artificial Pancreatic β Cell: Use of Proportional-Integral-Derivative Equivalent Model-Based Controllers" Journal of Diabetes Science and Technology, vol. 2, Issue 4, Jul. 2008.

(Continued)

*Primary Examiner* — Jason Flick

(57) ABSTRACT

Described and illustrated is a system for management of diabetes that includes an infusion pump, glucose sensor and controller with a method programmed into the controller. The infusion pump is configured to deliver insulin to a subject. The system provides the user with the ability to understand the effects of bolus insulin dosing upon their glucose levels. Specifically, the system provides a message that must include: (a) the trend of the user's glucose; (b) the recommended bolus; and (c) the actual bolus.

2 Claims, 5 Drawing Sheets

(56) References Cited

U.S. PATENT DOCUMENTS

| | | |
|---|---|---|
| 2011/0257627 A1 | 10/2011 | Hovorka |
| 2011/0313680 A1 | 12/2011 | Doyle, III et al. |
| 2012/0059237 A1 | 3/2012 | Amir et al. |
| 2012/0095318 A1 | 4/2012 | Galley et al. |
| 2014/0005633 A1* | 1/2014 | Finan .................. A61M 5/1723 604/504 |
| 2014/0074059 A1 | 3/2014 | Howell et al. |

OTHER PUBLICATIONS

Paola Soru et al., "MPC Based Artificial Pancreas; Strategies for Individualization and Meal Compensation" Annual Reviews in Control 36, p. 118-128 (2012).

Cobelli et al., "Artificial Pancreas: Past, Present, Future" Diabetes vol. 60, Nov. 2011.

Magni et al., "Run-to-Run Tuning of Model Predictive Control for Type 1 Diabetes Subjects: In Silico Trial" Journal of Diabetes Science and Technology, vol. 3, Issue 5, Sep. 2009.

Lee et al., "A Closed-Loop Artificial Pancreas Using Model Predictive Control and a Sliding Meal Size Estimator" Journal of Diabetes Science and Technology, vol. 3, Issue 5, Sep. 2009.

Lee et al., "A Closed-Loop Artificial Pancreas based on MPC: Human Friendly Identification and Automatic Meal Disturbance Rejection" Proceedings of the 17th World Congress, The International Federation of Automatic Control, Seoul Korea Jul. 6-11, 2008.

Magni et al., "Model Predictive Control of Type 1 Diabetes: An in Silico Trial" Journal of Diabetes Science and Technology, vol. 1, Issue 6, Nov. 2007.

Wang et al., "Automatic Bolus and Adaptive Basal Algorithm for the Artificial Pancreatic β-Cell" Diabetes Technology and Therapeutics, vol. 12, No. 11, 2010.

Percival et al., "Closed-Loop Control of an Artificial Pancreatic β-Cell Using Multi-Parametric Model Predictive Control" Diabetes Research 2008.

U.S. Appl. No. 13/834,571, filed Mar. 15, 2013.

International Search Report and Written Opinion issued in related International Patent Application No. PCT/US14/66095, dated Feb. 19, 2015.

Supplementary European Search Report issued in related European Patent Application No. 14867860.0, dated Jul. 19, 2017, 10 pages.

* cited by examiner

METHOD AND SYSTEM FOR MANAGEMENT OF DIABETES WITH A GLUCOSE MONITOR AND INFUSION PUMP TO PROVIDE FEEDBACK ON BOLUS DOSING

BACKGROUND

Diabetes mellitus is a chronic metabolic disorder caused by an inability of the pancreas to produce sufficient amounts of the hormone insulin, resulting in the decreased ability of the body to metabolize glucose. This failure leads to hyperglycemia, i.e. the presence of an excessive amount of glucose in the blood plasma. Persistent hyperglycemia and/or hypoinsulinemia has been associated with a variety of serious symptoms and life threatening long term complications such as dehydration, ketoacidosis, diabetic coma, cardiovascular diseases, chronic renal failure, retinal damage and nerve damages with the risk of amputation of extremities. Because restoration of endogenous insulin production is not yet possible, a permanent therapy is necessary which provides constant glycemic control in order to always maintain the level of blood glucose within normal limits. Such glycemic control is achieved by regularly supplying external insulin to the body of the patient to thereby reduce the elevated levels of blood glucose.

External biologic such as insulin was commonly administered by means of multiple daily injections of a mixture of rapid and intermediate acting drugs via a hypodermic syringe. It has been found that the degree of glycemic control achievable in this way is suboptimal because the delivery is unlike physiological hormone production, according to which hormone enters the bloodstream at a lower rate and over a more extended period of time. Improved glycemic control may be achieved by the so-called intensive hormone therapy which is based on multiple daily injections, including one or two injections per day of a long acting hormone for providing basal hormone and additional injections of rapidly acting hormone before each meal in an amount proportional to the size of the meal. Although traditional syringes have at least partly been replaced by insulin pens, the frequent injections are nevertheless very inconvenient for the patient, particularly those who are incapable of reliably self-administering injections.

Substantial improvements in diabetes therapy have been achieved by the development of the drug delivery device, relieving the patient of the need for syringes or drug pens and the administration of multiple daily injections. The drug delivery device allows for the delivery of drug in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Blood or interstitial glucose monitoring is required to achieve acceptable glycemic control. For example, delivery of suitable amounts of insulin by the drug delivery device requires that the patient frequently determines his or her blood glucose level and manually input this value into a user interface for the external pumps, which then calculates a suitable modification to the default or currently in-use insulin delivery protocol, i.e., dosage and timing, and subsequently communicates with the drug delivery device to adjust its operation accordingly. The determination of blood glucose concentration is typically performed by means of an episodic measuring device such as a hand-held electronic meter which receives blood samples via enzyme-based test strips and calculates the blood glucose value based on the enzymatic reaction.

Continuous glucose monitoring (CGM) has also been utilized over the last twenty years with drug delivery devices to allow for closed loop control of the insulin(s) being infused into the diabetic patients. To allow for closed-loop control of the infused insulins, proportional-integral-derivative ("PID") controllers have been utilized with mathematical model of the metabolic interactions between glucose and insulin in a person. The PID controllers can be tuned based on simple rules of the metabolic models. However, when the PID controllers are tuned or configured to aggressively regulate the blood glucose levels of a subject, overshooting of the set level can occur, which is often followed by oscillations, which is highly undesirable in the context of regulation of blood glucose. Alternative controllers were investigated. It was determined that a model predictive controller ("MPC") used in the petrochemical industries where processes involved large time delays and system responses, was the most suitable for the complex interplay between insulin, glucagon, and blood glucose. The MPC controller has been demonstrated to be more robust than PID because MPC considers the near future effects of control changes and constraints in determining the output of the MPC whereas PID typically involves only past outputs in determining future changes. Constraints can be implemented in the MPC controller such that MPC prevents the system from running away when the limit has already been reached. Another benefit of MPC controllers is that the model in the MPC can, in some cases, theoretically compensate for dynamic system changes whereas a feedback control, such as PID control, such dynamic compensation would not be possible.

MPC can be viewed therefore as a combination of feedback and feed forward control. MPC, however, typically requires a metabolic model to mimic as closely as possible the interaction between insulin and glucose in a biological system. As such, due to person-to-person biological variations, MPC models continue to be further refined and developed presently. As informational background on MPC relating to details of the MPC controllers, variations on the MPC, and mathematical models representing the complex interaction of glucose and insulin, all of which are shown and described in the following documents:

U.S. Pat. No. 7,060,059;
US Patent Application Nos. 2011/0313680 and 2011/0257627,
International Publication WO 2012/051344,
Percival et al., "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008.
Paola Soru et al., "*MPC Based Artificial Pancreas; Strategies for Individualization and Meal Compensation*" Annual Reviews in Control 36, p. 118-128 (2012), Cobelli et al., "*Artificial Pancreas: Past, Present, Future*" Diabetes Vol. 60, November 2011;

Magni et al., "*Run-to-Run Tuning of Model Predictive Control for Type 1 Diabetes Subjects: In Silico Trial*" Journal of Diabetes Science and Technology, Vol. 3, Issue 5, September 2009.

Lee et al., "*A Closed-Loop Artificial Pancreas Using Model Predictive Control and a Sliding Meal Size Estimator*" Journal of Diabetes Science and Technology, Vol. 3, Issue 5, September 2009;

Lee et al., "*A Closed-Loop Artificial Pancreas based on MPC: Human Friendly Identification and Automatic Meal Disturbance Rejection*" Proceedings of the 17th World Congress, The International Federation of Automatic Control, Seoul Korea Jul. 6-11, 2008;

Magni et al., "*Model Predictive Control of Type 1 Diabetes: An in Silico Trial*" Journal of Diabetes Science and Technology, Vol. 1, Issue 6, November 2007;

Wang et al., "*Automatic Bolus and Adaptive Basal Algorithm for the Artificial Pancreatic β-Cell*" Diabetes Technology and Therapeutics, Vol. 12, No. 11, 2010; and Percival et al., "*Closed-Loop Control of an Artificial Pancreatic β-Cell Using Multi-Parametric Model Predictive Control*" Diabetes Research 2008.

All articles or documents cited in this application are hereby incorporated by reference into this application as if fully set forth herein.

SUMMARY OF THE DISCLOSURE

Applicants have devised a technique that allows for a method for operating a diabetes management system to manage diabetes of a user. The system has an infusion pump, at least one glucose monitor and a controller. The method can be achieved by: determining a glucose measurement in which a fluid sample with glucose is transformed into enzymatic byproducts by application of electrical signals to the sample; calculating a bolus recommendation based on the glucose measurement made by the determining step; evaluating whether the bolus recommendation was followed by a user of the system; in the event the bolus recommendation was not followed by the user then: storing the actual bolus delivered by the infusion pump; measuring the glucose value in subsequent fluid samples and if the glucose values over time is greater than a predetermined high trend threshold then annunciating a high glucose trend, along with the recommended bolus and the actual bolus delivered by the pump otherwise if the glucose values over time is less than a predetermined low trend threshold then annunciating a low glucose trend along with both the recommended bolus and the actual bolus delivered by the pump.

In yet another aspect, a system for management of diabetes is provided that includes an episodic glucose meter, continuous glucose meter, and an infusion pump coupled to a controller. The episodic glucose meter is configured to measure glucose level in a fluid sample of a subject at discrete non-uniform time intervals and provide such episodic glucose level as input data for bolus calculation; a continuous glucose monitor to continuously measure glucose level of the subject at discrete, generally uniform time intervals and provide the glucose level at each interval in the form of glucose measurement data that can be used for bolus calculation. The insulin infusion pump is configured to deliver insulin to the subject; a microcontroller in communication with the pump, glucose meter and the glucose monitor. The controller is configured to provide a bolus recommendation to the subject, evaluate whether an actual bolus delivered by the pump is other than the bolus recommendation. In the event the actual bolus delivered is other than the bolus recommendation, the system determines a trend of glucose values over a period of time and annunciates one of a low trend or high trend to the user along with actual bolus delivered and bolus recommendation.

In each of the above aspects, the following features may also be utilized in combination with each of the aspects. For example, the system may store the glucose measurement made by the measuring step in the controller; the system may ascertain a need for another bolus recommendation; the system may determine a declining rate of change in the glucose measurements of fluid samples of the user; the glucose monitor may include a continuous glucose monitor; the annunciating of the high glucose trend may include displaying a message that a trend of glucose measurements is increasing after a bolus delivery along with both the recommended bolus and the actual bolus delivered; the annunciating of the low glucose trend may include displaying a textual message that a trend of glucose measurements is decreasing after a bolus delivery along with both the recommended bolus and the actual bolus delivered; the low trend threshold may include a decreasing or negative rate of change of 20 mg/dL per every thirty minutes and the high trend threshold may include an increasing or positive rate of change of 20 mg/dL per thirty minutes.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Furthermore, the term "user" includes not only the patient using a drug infusion device but also the caretakers (e.g., parent or guardian, nursing staff or home care employee). The term "drug" may include hormone, biologically active materials, pharmaceuticals or other chemicals that cause a biological response (e.g., glycemic response) in the body of a user or patient.

Figure 1:
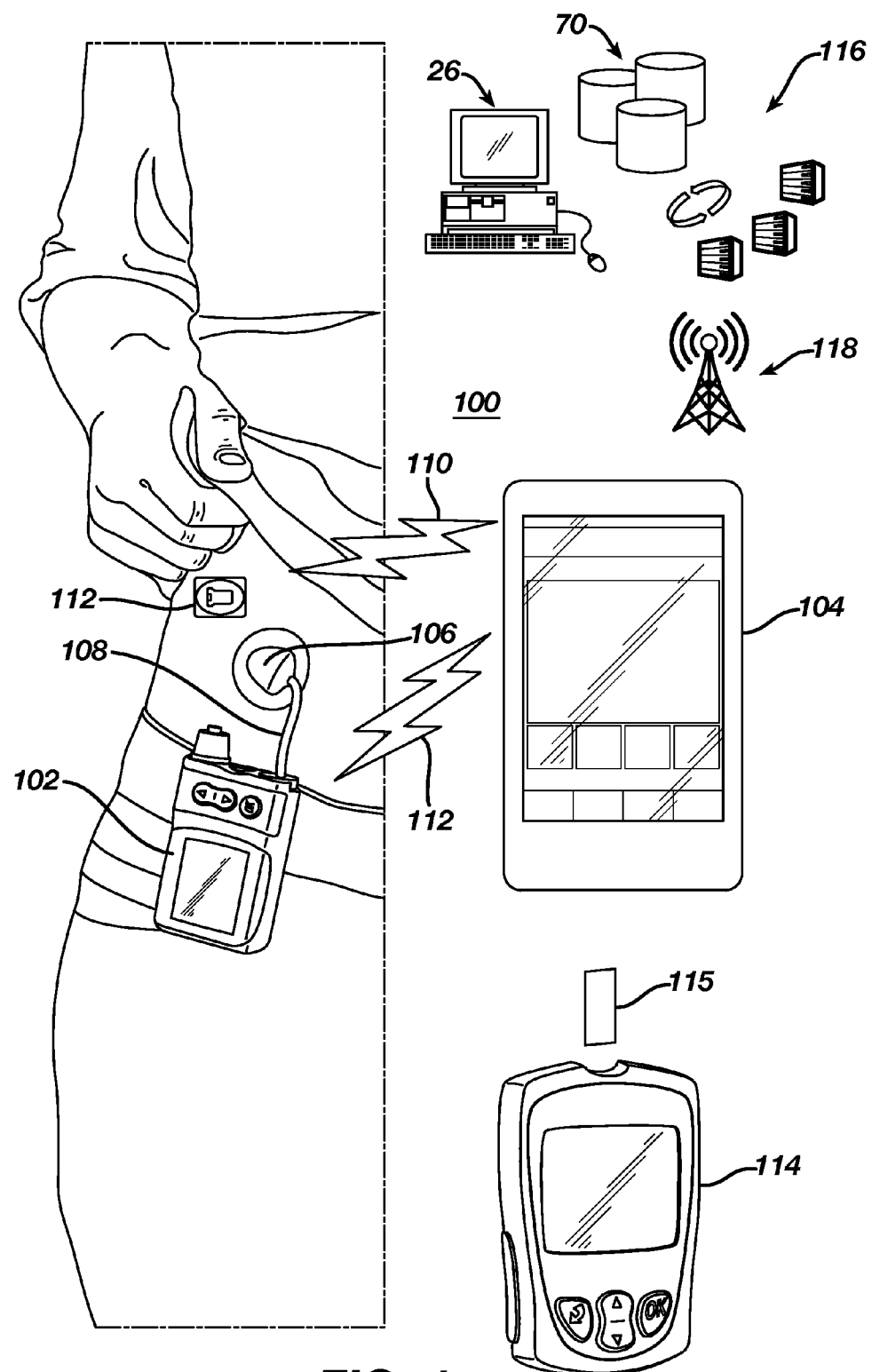
FIG. 1 illustrates the system in which a controller for the pump or glucose monitor(s) is separate from both the infusion pump and the glucose monitor(s) and in which a network can be coupled to the controller to provide near real-time monitoring.

FIG. 1 illustrates a drug delivery system 100 according to an exemplary embodiment that utilizes the principles of the invention. Drug delivery system 100 includes a drug delivery device 102 and a remote controller 104. Drug delivery device 102 is connected to an infusion set 106 via flexible tubing 108.

Drug delivery device 102 is configured to transmit and receive data to and from remote controller 104 by, for example, radio frequency communication 112. Drug delivery device 102 may also function as a stand-alone device with its own built in microcontroller. In one embodiment, drug delivery device 102 is an insulin infusion device and remote controller 104 is a hand-held portable controller. In such an embodiment, data transmitted from drug delivery device 102 to remote controller 104 may include information such as, for example, insulin delivery data, glucose information, basal, bolus, insulin to carbohydrates ratio or insulin sensitivity factor, to name a few. The microcontroller 104 is configured to include an MPC controller 10 that has been programmed to receive continuous glucose readings from a CGM sensor 112. Data transmitted from remote microcontroller 104 to insulin delivery device 102 may include glucose test results and a food database to allow the drug delivery device 102 to calculate the amount of insulin to be delivered by drug delivery device 102. Alternatively, the remote microcontroller 104 may perform basal dosing or bolus calculation and send the results of such calculations to the drug delivery device. In an alternative embodiment, an episodic blood glucose meter 114 may be used alone or in conjunction with the CGM sensor 112 to provide data to either or both of the microcontroller 104 and drug delivery device 102. Alternatively, the remote microcontroller 104 may be combined with the meter 114 into either (a) an integrated monolithic device; or (b) two separable devices that are dockable with each other to form an integrated device. Each of the devices 102, 104, and 114 has a suitable microcontroller (not shown for brevity) programmed to carry out various functionalities.

Drug delivery device 102 may also be configured for bi-directional wireless communication with a remote health monitoring station 116 through, for example, a wireless communication network 118. Remote controller 104 and remote monitoring station 116 may be configured for bi-directional wired communication through, for example, a telephone land based communication network. Remote monitoring station 116 may be used, for example, to download upgraded software to drug delivery device 102 and to process information from drug delivery device 102. Examples of remote monitoring station 116 may include, but are not limited to, a personal or networked computer 126, server 128 to a memory storage, a personal digital assistant, other mobile telephone, a hospital base monitoring station or a dedicated remote clinical monitoring station.

Drug delivery device 102 includes electronic signal processing components including a central processing unit and memory elements for storing control programs and operation data, a radio frequency module 116 for sending and receiving communication signals (i.e., messages) to/from remote controller 104, a display for providing operational information to the user, a plurality of navigational buttons for the user to input information, a battery for providing power to the system, an alarm (e.g., visual, auditory or tactile) for providing feedback to the user, a vibrator for providing feedback to the user, a drug delivery mechanism (e.g. a drug pump and drive mechanism) for forcing insulin from an insulin reservoir (e.g., an insulin cartridge) through a side port connected to an infusion set 108/106 and into the body of the user. An example of a drug delivery device 102 (or pump 16) can be in the form of a modified Animas Vibe insulin pump manufactured by Animas Corporation in Wayne, Pa. USA.

Glucose levels or concentrations can be determined by the use of the CGM sensor 112. The CGM sensor 112 utilizes amperometric electrochemical sensor technology to measure glucose with three electrodes operably connected to the sensor electronics and are covered by a sensing membrane and a biointerface membrane, which are attached by a clip.

The top ends of the electrodes are in contact with an electrolyte phase (not shown), which is a free-flowing fluid phase disposed between the sensing membrane and the electrodes. The sensing membrane may include an enzyme, e.g., glucose oxidase, which covers the electrolyte phase. In this exemplary sensor, the counter electrode is provided to balance the current generated by the species being measured at the working electrode. In the case of a glucose oxidase based glucose sensor, the species being measured at the working electrode is $H_2O_2$. The current that is produced at the working electrode (and flows through the circuitry to the counter electrode) is proportional to the diffusional flux of $H_2O_2$ generated by this electrochemical transformation of glucose into its enzymatic byproducts. Accordingly, a raw signal may be produced that is representative of the concentration of glucose in the user's body, and therefore may be utilized to estimate a meaningful glucose value. Details of the sensor and associated components are shown and described in U.S. Pat. No. 7,276,029, which is incorporated by reference herein as if fully set forth herein this application. In one embodiment, a continuous glucose sensor from the Dexcom Seven System® (manufactured by Dexcom Inc.) can also be utilized with the exemplary embodiments described herein.

In one embodiment of the invention, the following components can also be utilized as a system for management of diabetes that is akin to an artificial pancreas: OneTouch Ping® Glucose Management System by Animas Corporation that includes at least an infusion pump and an episodic glucose sensor; and DexCom® G4 Platinum® CGM by DexCom Corporation with interface to connect these components and programmed in MATLAB®language and accessory hardware to connect the components together; and control algorithms in the form of an MPC that automatically regulates the rate of insulin delivery based on the glucose level of the patient, historical glucose measurement and anticipated future glucose trends, and patient specific information.

Figure 2:
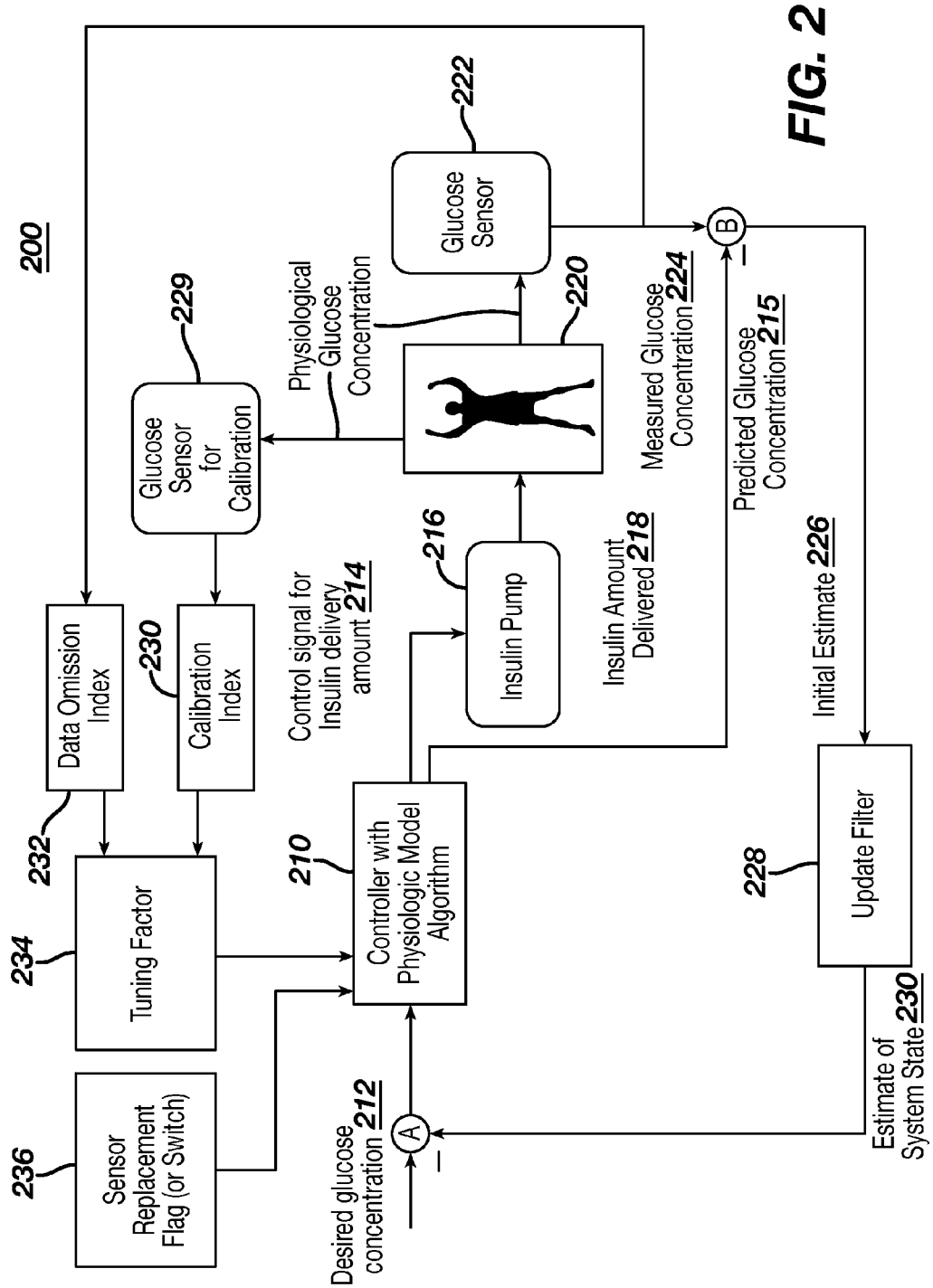
FIG. 2 illustrates an exemplary embodiment of the diabetic management system in schematic form.

FIG. 2 illustrates a schematic diagram 200 of the system 100 in FIG. 1 programmed with the solution devised by applicants to counteract a less than desirable effect of a closed-loop control system. In particular, FIG. 2 provides for an MPC programmed into a control logic module 10 that is utilized in controller 104. MPC logic module 10 receives a desired glucose concentration or range of glucose concentration 12 (along with any modification from an update filter 28 so that it is able to maintain the output (i.e., glucose level) of the subject within the desired range of glucose levels.

Referring to FIG. 2, the first output 14 of the MPC-enabled control logic 10 can be a control signal to an insulin pump 16 to deliver a desired quantity of insulin 18 into a subject 20 at predetermined time intervals, which can be indexed every 5 minutes using time interval index k. A second output in the form of a predicted glucose value 15 can be utilized in control junction B. A glucose sensor 22 (or 112 in FIG. 1) measures the glucose levels in the subject 20 in order to provide signals 24 representative of the actual or measured glucose levels to control junction B, which takes the difference between measured glucose concentration 24 and the MPC predictions of that measured glucose concentration. This difference provides input for the update filter 26 of state variables of the model. The difference 26 is provided to an estimator (also known as an update filter 28) that provides for estimate of state variables of the model that cannot be measured directly. The update filter 28 is preferably a recursive filter in the form of a Kalman filter with tuning parameters for the model. The output of the update or recursive filter 28 is provided to control junction A whose output is utilized by the MPC in the control logic 10 to further refine the control signal 14 to the pump 16 (or 102 in FIG. 1). A tuning factor 34 is used with the MPC controller 10 to "tune" the controller in its delivery of the insulin. To accomplish this, applicants have devised the use of a calibration index module 30 and data omission module 32 to adjust the tuning factor. Calibration index module 30 is configured to track the number of glucose measurement calibration, which is typically accomplished by an episodic glucose monitor, such as, for example, a blood glucose test strip and meter system. Data omission index module 32 is configured to track the number of missing measurements or data from the continuous glucose monitor 22.

Details of the closed-loop controller are provided in U.S. patent application Publication No. 20140276554 filed on Mar. 15, 2013 which is hereby incorporated by reference as if fully set forth herein.

Figure 3:
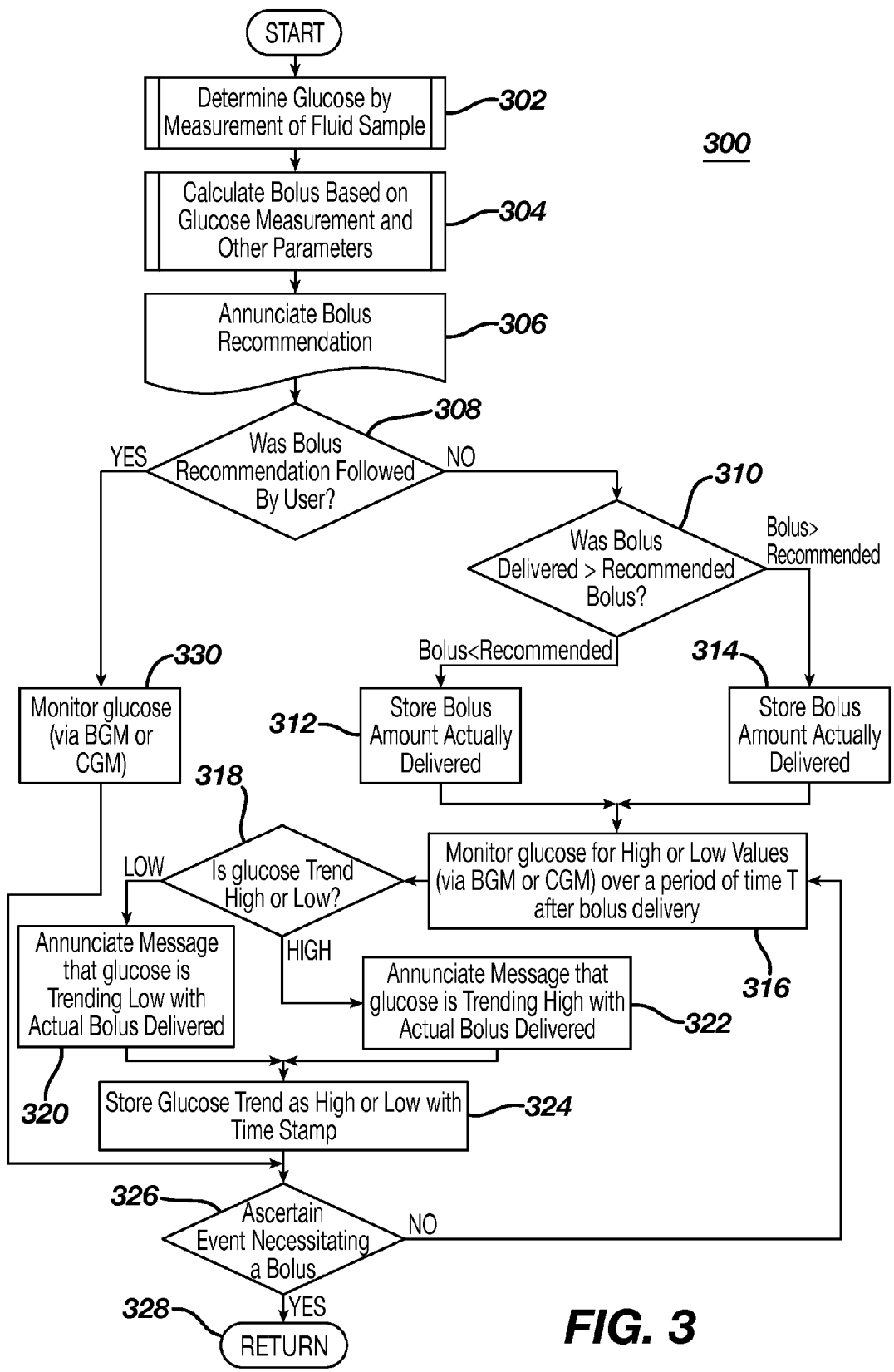
FIG. 3 illustrates the logic utilized in the controller of FIG. 1 or FIG. 2.
Figure 4A:
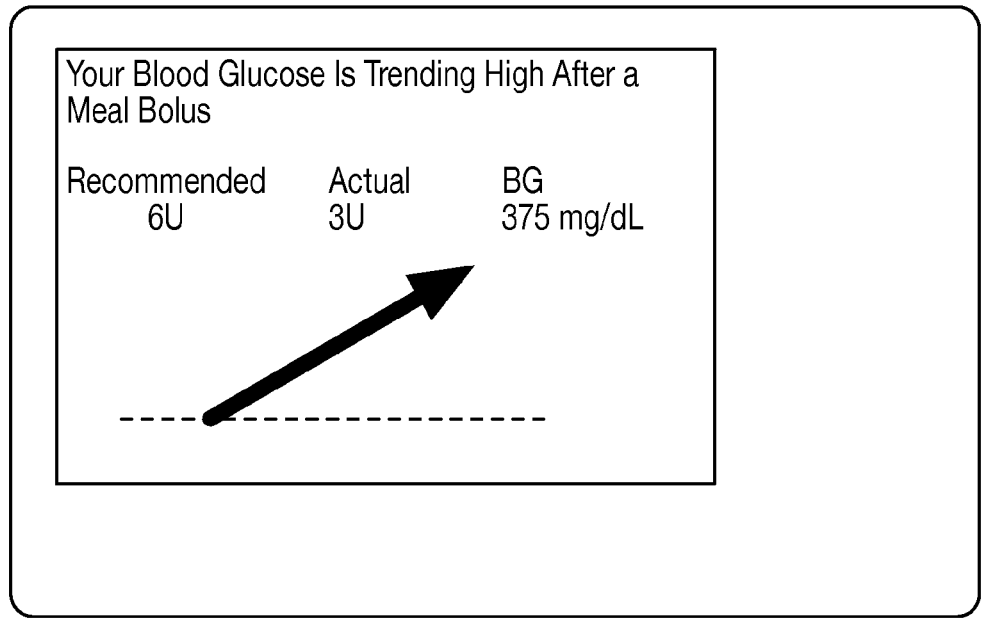
FIGS. 4A and 4B illustrate messages from the system.
Figure 4B:
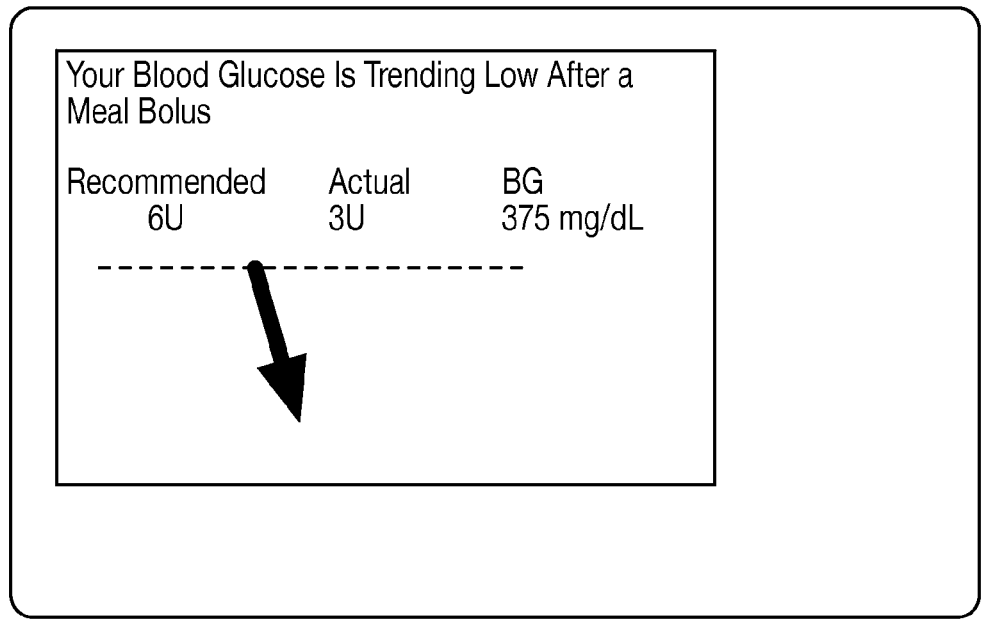
Figure 5:
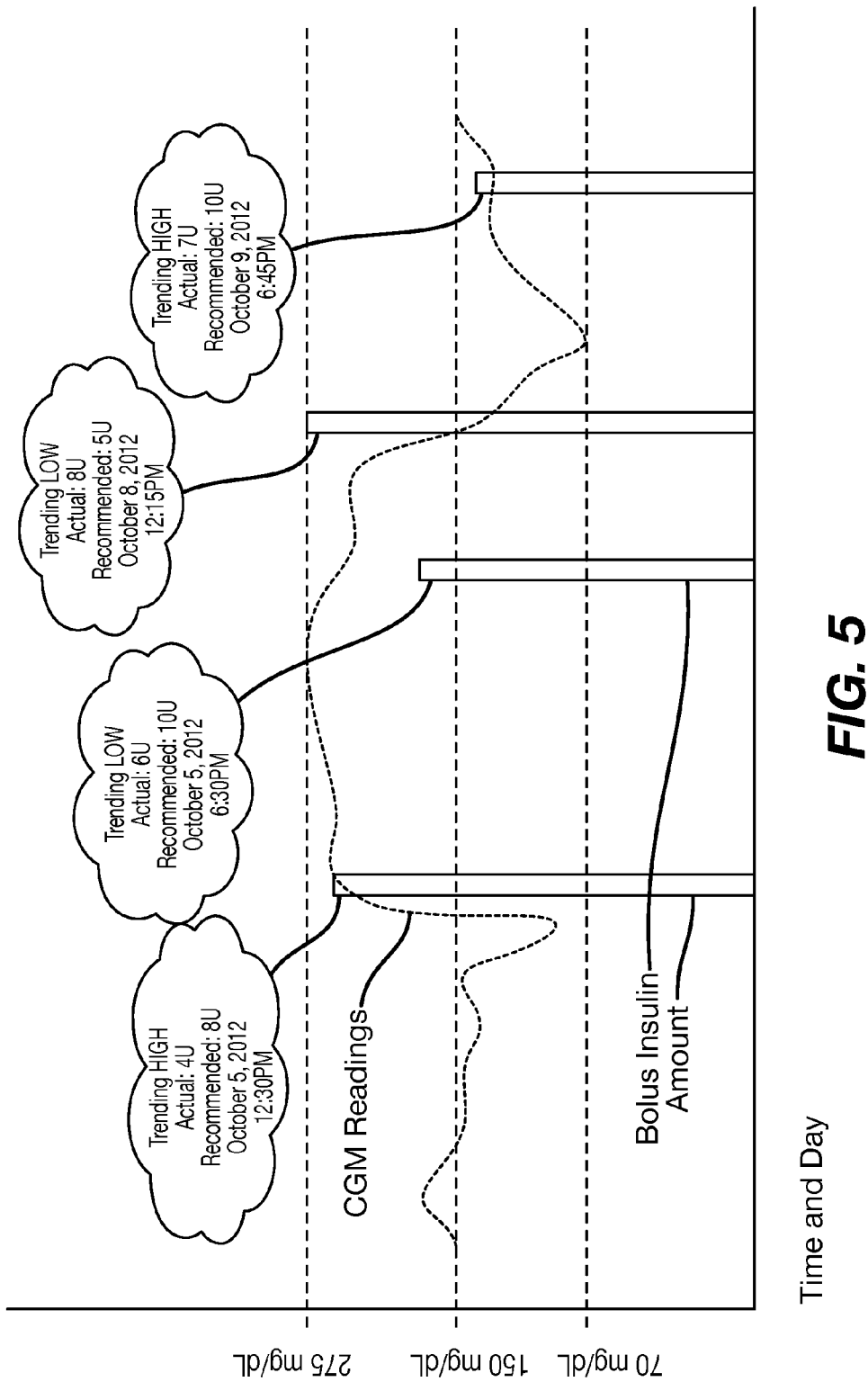
FIG. 5 illustrates a graphical and textual message of the system.

FIG. 3 illustrates logical process 300 that can be utilized (with appropriate modifications that are well within the capabilities of one skilled in the field) for either system 100 or system 200. Process 300 starts with a decision (by the user or the controller) at step 302 to conduct a glucose measurement in a fluid sample (e.g., blood or interstitial fluid). The glucose in the fluid sample is then physically transformed into enzymatic byproducts due to the electrochemical reaction with the enzyme on the glucose sensing electrodes. At step 304, a bolus amount of insulin is calculated. The insulin bolus calculation is known in the art, such as, for example, shown and described in US Patent Application Publication 20120095318 or U.S. Pat. Nos. 6,872,200, 7,815,602, 7,819, 843. At step 306, the calculated bolus is annunciated as a recommended bolus to the user. At step 308, the system checks to see if the user confirmed delivery of the recommended bolus amount. If not, the system checks the pump at step 310 to determine the amount actually infused to the user. At step 312, if the insulin amount actually infused is less than the recommended amount, the system stores this amount. At step 314, if the actual amount of insulin infused is greater than the recommended, this again is stored. At step 316, the system monitors the continuous glucose readings for a period of time T after the bolus delivery. After time T, the system checks at step 318 to see the rate of change of glucose readings is trending higher or lower. If the rate of change is trending lower then the system annunciate a message at step 320 to the user that: (a) the glucose readings are trending low with respect to a predetermined low trend threshold of, for example, such as a negative decrease of about 20 mg/dL for every thirty minutes; (b) actual amount of bolus delivered and (c) recommended bolus. On the other hand, if the rate of change of the glucose values are increasing then the system annunciate a message at step 322 that: (a) the glucose is trending higher with respect to a predetermined high trend threshold, such as, for example, a positive increase of about 20 mg/dL for every thirty minutes, (b) actual bolus amount delivered; and (c) recommended amount. It should be understood that the blood glucose concentration of 20 mg/dL and the time interval of thirty minutes are only examples and other blood glucose concentrations and time durations are within the scope of the claimed invention. The messages provided at respective steps 320 and 322 can be in the form shown in FIGS. 4A and 4B on the controller or on the pump. Alternatively, the messages can be graphical and textual as shown in FIG. 5. At step 324, the system stores the rate of change (or a flag for high trend or low trend) along with the time stamp. At step 326, the system determines (via monitoring of the CGM or by user input) that there is a life event (e.g., meals, snacks, exercise, drinks, and the like) that may necessitate another bolus calculation. If such is the case, the system returns to the main routine at step 328 otherwise, the system continues monitoring the glucose levels at step 316.

Benefits of the invention are many: for example, the user is able to obtain a clear indication of the effects of insulin dosing on the user's glucose level; the system provides nearly instantaneous feedback to the user of the user's glucose level after a bolus dosing so that the user would be able to determine if their recommended bolus should be followed or a dosing that is different from the recommended bolus is better for the user.

While the invention has been described in terms of particular variations and illustrative figures, those of ordinary skill in the art will recognize that the invention is not limited to the variations or figures described. For example, the closed-loop controller need not be an MPC controller but can be, with appropriate modifications by those skilled in the art, a PID controller, a PID controller with internal model control (IMC), a model-algorithmic-control (MAC) that are discussed by Percival et al., in "*Closed-Loop Control and Advisory Mode Evaluation of an Artificial Pancreatic β Cell: Use of Proportional-Integral-Derivative Equivalent Model-Based Controllers*" Journal of Diabetes Science and Technology, Vol. 2, Issue 4, July 2008. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A system for management of diabetes, the system comprising:
    an episodic glucose meter to measure glucose level in a fluid sample of a subject at discrete non-uniform time intervals and provide such episodic glucose level as input data for calculating a bolus recommendation;
    a continuous glucose monitor to continuously measure glucose level of the subject at discrete generally uniform time intervals and provide the glucose level at each interval in the form of glucose measurement data that can be used for calculating the bolus recommendation;
    an insulin infusion pump to deliver insulin to the subject;
    a microcontroller in communication with the pump, glucose meter and the glucose monitor in which the microcontroller is configured to provide the bolus recommendation to the subject, evaluate whether an actual bolus delivered by the pump is other than the bolus recommendation; in the event the actual bolus delivered is other than the bolus recommendation, determine a trend of glucose values over a period of time and annunciate one of a low trend or high trend to the user simultaneously with the actual bolus delivered and the bolus recommendation.

2. The system of claim 1, in which the low trend threshold comprises a decreasing rate of glucose concentration about 20 mg/dL every thirty minutes and the high trend threshold comprises an increasing rate of change of glucose concentration of about 20 mg/dL every thirty minutes.

\* \* \* \* \*